(12) United States Patent
Gollobin

(10) Patent No.: US 7,736,341 B2
(45) Date of Patent: Jun. 15, 2010

(54) PROTECTIVE SHEATH FOR WINGED NEEDLE WITH KEYHOLE FOR RELEASABLY RETAINING TUBING AND PACKAGING INCORPORATING SAME

(76) Inventor: Peter Gollobin, 72 E. Second St., Mineola, NY (US) 11501

( * ) Notice: Subject to any disclaimer, the term of this patent is extended or adjusted under 35 U.S.C. 154(b) by 260 days.

(21) Appl. No.: 11/544,435

(22) Filed: Oct. 5, 2006

(65) Prior Publication Data

US 2007/0093758 A1 Apr. 26, 2007

(51) Int. Cl.
*A61M 5/00* (2006.01)
*B65D 71/00* (2006.01)
*B65D 83/10* (2006.01)

(52) U.S. Cl. .................. 604/171; 206/364; 206/571
(58) Field of Classification Search ............ 206/53, 206/225, 305, 306, 413, 364, 438, 571; 24/122.3, 24/16 R; 600/585; 604/103.04, 171, 192, 604/536
See application file for complete search history.

(56) References Cited

U.S. PATENT DOCUMENTS

| | | | |
|---|---|---|---|
| 3,926,309 A * | 12/1975 | Center | 206/364 |
| 4,149,635 A * | 4/1979 | Stevens | 206/370 |
| 4,379,506 A * | 4/1983 | Davidson | 206/364 |
| 4,850,954 A * | 7/1989 | Charvin | 604/6.14 |
| 5,226,530 A * | 7/1993 | Golden | 206/210 |
| 5,947,284 A * | 9/1999 | Foster | 206/364 |
| 6,053,313 A * | 4/2000 | Farrell et al. | 206/364 |
| 6,090,073 A * | 7/2000 | Gill | 604/164.01 |
| 6,387,086 B2 * | 5/2002 | Mathias et al. | 604/409 |
| 7,334,678 B2 * | 2/2008 | Kesler et al. | 206/364 |
| 2002/0188260 A1 * | 12/2002 | Gollobin | 604/263 |
| 2004/0055926 A1 * | 3/2004 | Duffy et al. | 206/571 |

* cited by examiner

*Primary Examiner*—Nicholas D Lucchesi
*Assistant Examiner*—Nathan R Price
(74) *Attorney, Agent, or Firm*—Galgano & Associates, PLLC; Thomas M. Galgano; Jessica G. Bower

(57) ABSTRACT

A protective sheath for a winged needle has a hilt with a keyhole for releasably receiving a length of tubing. Methods of the invention include forming a U-shaped bend in the tubing and inserting it into the keyhole prior to packaging.

5 Claims, 3 Drawing Sheets

PROTECTIVE SHEATH FOR WINGED NEEDLE WITH KEYHOLE FOR RELEASABLY RETAINING TUBING AND PACKAGING INCORPORATING SAME

This application is related to co-owned U.S. Pat. No. 5,330,438, and published application number 20020188260, the complete disclosures of which are hereby incorporated herein by reference.

BACKGROUND OF THE INVENTION

1. Field of the Invention

The present invention relates to a protective sheath or safety guard for winged needles and, in particular, to a protective sheath having a keyhole for releasably retaining the flexible tubing of a winged needle set and a method of packaging a winged needle set having such a protective sheath.

2. State of the Art

A well known winged needle (also known as a butterfly needle) assembly is shown in prior art FIG. 1. The assembly 10 includes a needle 12 having a pair of wings 14, coupled to a first end of a length of coiled flexible tubing 16, and a coupling attached to the rear end of the tubing by which this winged needle set or assembly may be attached to, e.g., means for piercing a vacuum bottle for blood collecting or a Luer lock tapered coupling for IV tubing. The winged needle assembly has been used for many years in, e.g., the administration of IV medications and in obtaining blood samples when use in conjunction with vacuum bottles. The purpose of the assembly is to limit trauma to the patient's blood vessel(s), particularly-when multiple samples of blood are to be taken or when multiple types of medication are to be administered. After the needle is inserted into the patient's blood vessel, the wings are taped to the patient's body to prevent movement of the needle when coupling/uncoupling the Luer lock or attaching or disconnecting the vacuum bottle used for blood collecting. Any movement of the needle can cause trauma of the patient's blood vessel. The winged needle assemblies are typically packaged with the flexible tubing wound in a coil such as illustrated in FIG. 1, typically coiled in several loops. It has recently been discovered by the inventor herein that when a winged needle kit is packaged with the tubing coiled, the tubing tends to retain a coiled configuration even after it is unpackaged. It has also been discovered by the inventor herein that when the flexible tubing has retained a coiled configuration, even a slight movement of one end of the tubing will disadvantageously cause immediate movement of the other end.

In the 1980s after the discovery of the HIV virus which causes AIDS, much attention was given to the problem of accidental needlesticks from contaminated medical equipment such as syringes and IV equipment, which poses serious risks to healthcare professionals. Even maintenance personnel who dispose of the used medical equipment are at risk. Hepatitis, AIDS and other diseases can be, and sometimes are, transmitted by accidental needlesticks from needles used on infected patients.

My prior U.S. Pat. No. 5,330,438 discloses an improved sheath construction (shown in prior art FIG. 2) which significantly minimizes the possibility of improper operation and jamming of the used needle relative to the sheath during the sheathing operation. The IV infusion set 20 includes an IV tube 22, a hollow needle 24 coupled to one end of the tube and two wings 26 adjacent the needle 24. A Luer connector (not shown) is connected to the other end of the IV tube. The IV infusion set 20 also includes a sheath 28 slidably disposed on tube 22. The sheath 28 is adapted to be slid past the flexible wings 26 to cover the needle after the needle has been used.

The sheath 28 preferably includes a knurled, generally cylindrical, annular base 29 by which the sheath may be easily grasped. Base 29 has a central bore (not shown) through which tube 22 may slidably pass and is integrally joined to a hollow generally tubular body 30 having a forward end 32 oriented toward the needle 24 and a rearward end 34 oriented away from the needle. The body 30 preferably has four fingers 35 separated by four longitudinally extending slots 36 extending from the forward end or tip 32 of body 30 to the rearward end 34. The slots 36 are each adapted to receive only one of the wings 26 to allow at least part of the sheath 28 to be slid past the wings 26 to cover the needle 24.

The body 30 also includes cutouts 42 at the rearward end of the slots 36, adapted to receive and engage the wings 26 to lock the sheath in its position covering the needle. The cutouts 42 have a width approximately equal to the width of one of the wings 26. Slot 36 is slightly narrower than the thickness of the wings. As a result, as the wings 26 pass through the slots 36, the fingers 35 will resiliently wedge apart, and upon passage of the wings 26 into the wider cutouts 42, snap back and assume their normal position, thereby trapping the wings 26 in the cutouts 42 behind the forward edges 44 of the cutouts. This prevents the needle 24 from sliding forwardly out of the sheath 28.

Recently, the U.S. Food and Drug Administration has requested that all safety devices used with needles either change color or produce an audible sound or provide some other easy to recognize evidence that the needle has been rendered safe. My prior application 20020188260 addresses that concern and provides other improvements.

FIGS. 3 and 4 illustrate the needle sheath of said published application. The sheath 128 is provided in conjunction with a hollow needle 124 with a pair of wings 126. The sheath 128 includes at least a pair of fingers 132, 140 extending from an annular base 130. (FIG. 4 illustrates an embodiment 128' with four fingers 132', 133, 140', 141). The fingers define a pair of slots 142 through which the wings 126 of the needle 124 may slide. The slots define an open end 146 and a closed end 154. The slots 142 are provided with a Z-bend 153, 155. The Z-bend is dimensioned such that the wings 126 can pass through it with some deformation, and an audible click is heard as the wings and/or fingers cease to be deformed. As seen in FIG. 3, the fingers 132, 140 terminate in a first annular structure 138 which is separated from the annular base 130 by a hilt 134. As shown in FIG. 3, the hilt 134 has two angled ends 150, 152, although the angled ends may be omitted as shown in FIG. 4 at 134'. The hilt 134 assists in holding the sheath while sliding the sheath and of the wings into the locked position shown in FIG. 3.

SUMMARY OF THE INVENTION

Accordingly, it is an object of the present invention to overcome the disadvantages imposed by packaging a winged needle and tube assembly with the tubing coiled.

It is a further object of the present invention to include the advantages of my prior inventions.

The foregoing and related objects are readily achieved in a winged needle and tube assembly of the type including a length of flexible tube with a hollow needle at one end, and a pair of outwardly projecting flexible wings adjacent the end of the tubing with the needle and a sheath slidably disposed on the tube and adapted to be slid over the needle to cover the needle after use. The sheath comprises a hollow generally tubular body having a forward end oriented toward the needle and a rearward end oriented away from the needle. The body has at least two longitudinally extending fingers separated by slots extending from the forward end of the body toward the rearward end, each of the slots being dimensioned to receive only one of the wings to allow at least part of said sheath to be slid past the wings to cover the needle. The sheath is provided with a hilt which facilitates the sliding of the sheath and/or wings into a locked position where the sheath covers the needle. According to the invention, the hilt is provided with at least one keyhole for removably securing the flexible tubing.

Certain of the foregoing and related objects are attained according to the invention by the provision of a winged needle set, comprising a winged needle, a length of flexible tubing having first and second ends, said first end coupled to said needle, and a protective sheath slidably disposed on said tubing, said sheath having a hilt with said hilt having a keyhole dimensioned to releasably retain said tubing. Preferably, the winged needle set additionally includes a connector coupled to said second end of said flexible tubing and said hilt has two keyholes, each on opposite sides of said hilt.

Advantageously, the sheath comprises a hollow generally tubular body having a forward end oriented toward the needle and a rearward end oriented away from the needle with said body having at least two fingers defining slots through which said flexible wings slide. Most desirably, at least one of said wings slides into a locked position. The tubular body preferably has four fingers and four slots, each of said slots being provided with a Z-bend and the forward end of said fingers are V-shaped and tapered to facilitate the passage of said wings into the slots. Most advantageously, the sheath includes means for locking the sheath in a position covering the needle to prevent needlesticks from the needle.

Certain of the foregoing and related objects are also attained in a method of packaging a flexible tubing coupled to a winged needle having a protective sheath slidably mounted on said tubing having a hilt with a keyhole, comprising the steps of: forming a U-shaped bend in the length of flexible tubing, and inserting a section of the flexible tubing into the keyhole of the protective sheath so as to maintain the U-shaped bend. Most advantageously, the U-shaped bend is formed at the approximate midpoint of the tubing. Preferably, the method involves the further steps of positioning said sheath adjacent to said U-shaped bend, placing the tubing, needle, and sheath into a package, and sealing the package.

Certain of the foregoing and related objects are also attained in a protective sheath for a winged needle according to the invention which sheath comprises a hollow generally tubular body having a forward end oriented toward the needle and a rearward end oriented away from the needle, said body having at least two fingers defining slots, and a hilt at the rearward end of said body, said hilt defining at least one keyhole adapted to releasably receive a length of flexible tubing. Preferable, the sheath has means for locking said winged needle within said tubular body of said sheath and said tubular body has four fingers and four slots, each of said slots being provided with a Z-shaped bend.

In a-preferred embodiment of the invention, the forward end of said fingers are V-shaped and tapered to facilitate the passage of said wings into the slots and said sheath includes means for locking the sheath in a position covering the needle to prevent needlesticks from the needle. The tubing is preferably made of medical grade plastic tubing.

The invention is based on two discoveries, the first being the recognition of a problem not previously recognized, i.e., that the coiled shape retained by flexible medical tubing (e.g., IV tubing) which is coiled in its package causes the ends of the tubing to be mechanically responsive to each other. Movement of one end of a coiled IV tube causes immediate movement of the other end. The second discovery is that when the flexible tubing is packaged with only a single U-shaped bend, it retains its flexibility so that relatively large movement of one end has very little effect on the other end, i.e., movement of one end doesn't cause appreciable movement of the other end. This, in turn, reduces possible trauma to the injection site (patient's blood vessel) caused by movement of the needle.

Additional objects and advantages of the invention will become apparent to those skilled in the art upon reference to the detailed description taken in conjunction with the provided figures.

DETAILED DESCRIPTION OF THE PREFERRED EMBODIMENTS

Figure 1:
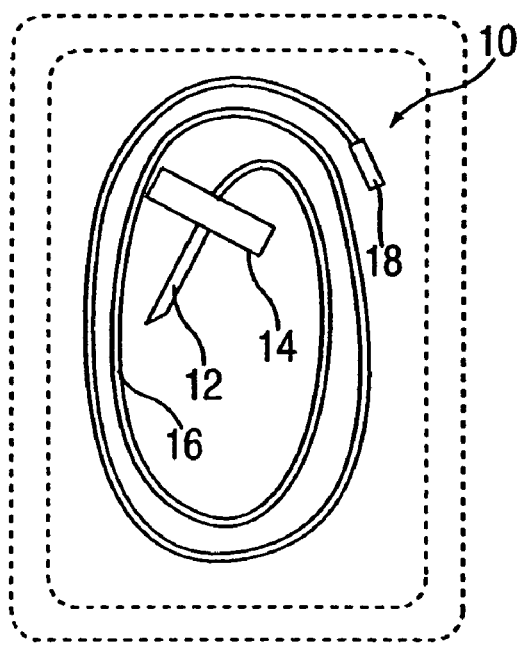
FIG. 1 is a plan view of a conventional IV infusion set having a winged needle.
Figure 2:
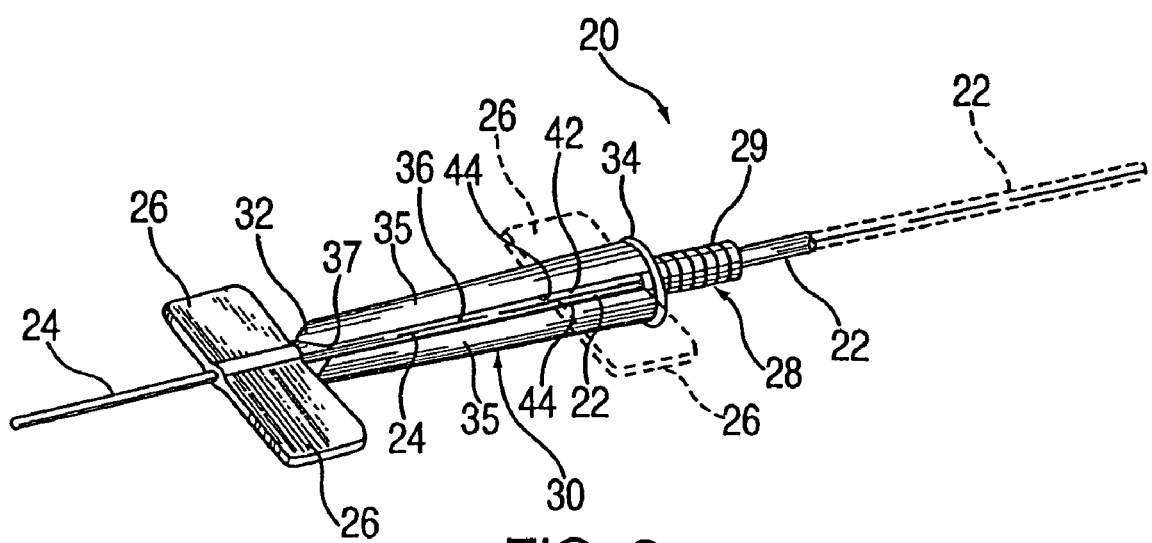
FIG. 2 is a perspective view of a winged needle and protective sheath according to my prior patent.
Figure 3:
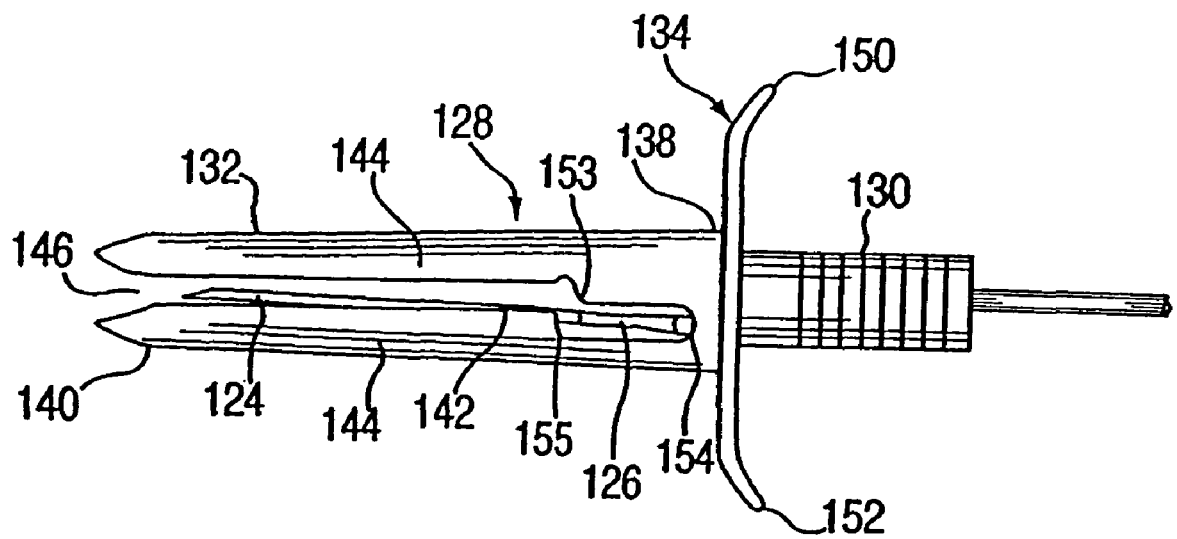
FIG. 3 is a side elevation view of a sheath according to my previously incorporated published application with the wings of a winged needle beyond the Z-bend in the slot of the sheath and thus in a locked position.
Figure 4:
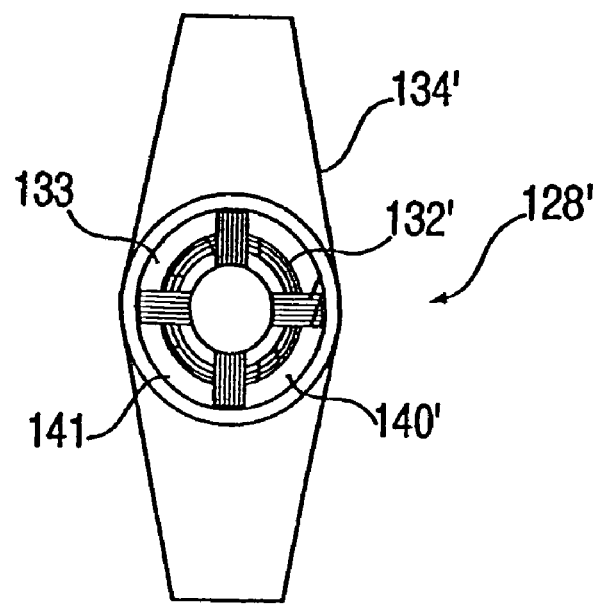
FIG. 4 is an end view of a sheath according to my previously incorporated published application with a slightly different shaped hilt.
Figure 5:
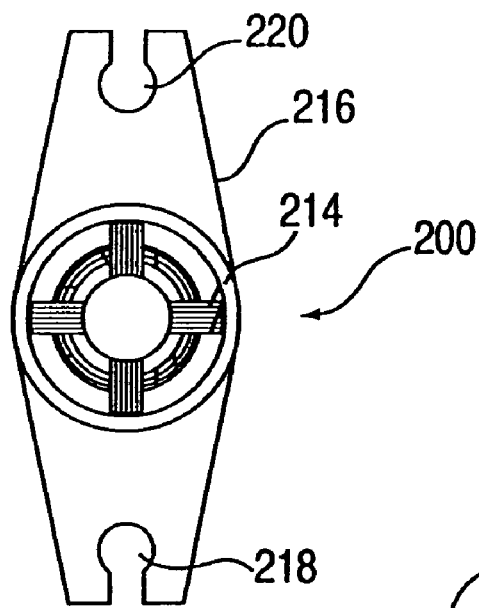
FIG. 5 is a view similar to FIG. 4 but illustrating the hilt according to the present invention.
Figure 6:
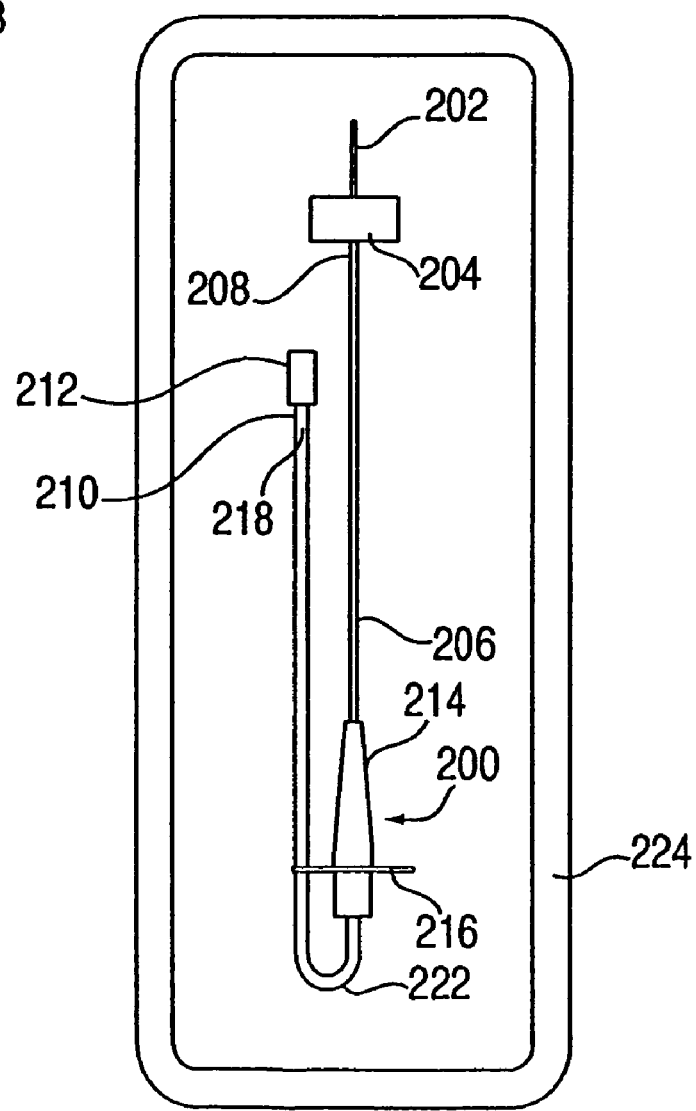
FIG. 6 is a plan view of a winged needle set according to the invention illustrating a method of using the hilt keyhole and a method of packaging the set.

Referring now to FIGS. 5 and 6, a winged needle set 200 according to the invention is shown which can be used in the medical field as, e.g., an IV infusion or blood collecting set. The winged needle set 200 includes a needle 202 having a pair of wings 204, and a length of medical grade, plastic flexible tubing 206. The tubing 206 has a first end 208 which is coupled to the needle 202 and a second end 210 which is typically coupled to a connector 212, e.g., a Luer lock tapered coupling for IV tubing or a threaded connector coupled to a needle for piercing a blood-collecting bottle. A protective sheath 214 having a hilt 216 is slidably disposed on the tubing 206. According to the present invention, the hilt 216 is provided with a first keyhole 218, and preferably also a second keyhole 220 as illustrated in FIG. 5. The characteristics of the winged needle set 200, other than the keyholes, are substantially the same as described in my previously incorporated published application.

According to methods of the invention, the flexible tubing 206 is bent approximately in half to define a U-shaped bend 222 and the sheath 214 is moved or shifted along tubing 206 to a position adjacent to the U-shaped bend 222. A portion or section of the tubing 206 adjacent the U-shaped bend 222 is inserted into one of the keyholes, e.g., 218 as shown in FIG. 6. This maintains the tubing with this U-shaped bend 222 at a location approximately midway between the first end 208 and the second end 210 of the tubing 206. Due to the size of the hilt, this bend 222 has a relatively small diameter. With the winged needle set 200 so configured, it is placed in a substantially rectangular package 224. The package may be made of any suitable sterile barrier material.

By pushing the flexible tubing into the keyhole before packaging, it forces the originally straight tubing to remain in a U-shape consisting of two straight lengths and one small diameter bend 222 at the approximate midpoint of the tubing 206. When the flexible tubing 206 is forced to remain in the same shape for a prolonged period of time, especially during the conditions of most sterility processes, it tends to retain most of the shape. Therefore, when the winged needle set 200 is removed from its package 224, and the flexible tubing 206 is pulled free from the keyhole 218, the flexible tubing 206 will remain with the shape of two straight lengths and one small diameter bend 222 at the approximate midpoint of the tubing 206.

The keyhole provides a fast, easy, and inexpensive method to produce the above-described U-shape in the tubing. It also changes the entire assembly into a long thin shape rather than a short fat coil shape. This long thin shape is easy to handle with standard packaging machinery. Most brands of winged needle sets are coiled and slid into a separate plastic sleeve to hold it in a workable shape so that it can be easily handled and transferred into standard packaging machines. The present invention reduces the cost of packaging because: there is no need to coil the tubing; there is no need to purchase and cut-to-length plastic sleeving; and there is no need to place the coiled tubing into a plastic sleeve prior to packaging.

According to the present invention, the tubing is quickly snapped into the keyhole on either side of the hilt, giving the tubing a workable "U" shape which can then easily be placed into a packaging machine or directly into the package.

There has been described and illustrated herein a protective sheath for butterfly or winged needles, a winged needle set, and methods for packaging the set. While particular embodiments of the invention have been described, it is not intended that the invention be limited thereto, as it is intended that the invention be as broad in scope as the art will allow and that the specification be read likewise. It will therefore be appreciated by those skilled in the art that yet other modifications could be made to the provided invention without deviating from its spirit and scope as so claimed.

The invention claimed is:

1. A method of packaging a flexible tubing coupled to a winged needle having a protective sheath slidably mounted on said tubing, comprising the steps of:

providing a winged needle for insertion into a patient, of a type comprising a length of flexible tubing having first and second ends, with a hollow needle at one end, and a pair of outwardly projecting flexible wings adjacent the end of the tubing with the needle, and having a protective sheath slidably disposed on said length of flexible tubing which is adapted to be slid past the wings to cover the needle after use in a patient, to minimize risk of accidental needle sticks, said protective sheath comprising a hollow generally tubular body having slots formed therein, through which said flexible wings slide, wherein at least one of said wings slides into a locked position and wherein said sheath has a hilt with at least one keyhole formed therein which is dimensioned to releasably retain said tubing therein;

forming a single U-shaped bend in the length of flexible tubing;

maintaining the U-shaped bend in the flexible tubing by inserting a section of said flexible tubing into one of said keyholes so as to minimize risk of the tubing from retaining a coiled configuration when said tubing is removed from a packaging; and placing said tubing, needle, and sheath into a package so that said flexible tubing is retained in one of said keyholes and said U-shaped bend is maintained in said flexible tubing.

2. The method according to claim 1, wherein said U-shaped bend is formed at the approximate midpoint of the tubing.

3. The method according to claim 2, further comprising the step of positioning said sheath adjacent to said U-shaped bend.

4. The method according to claim 2, further comprising the step of placing the tubing, needle, and sheath into a package.

5. The method according to claim 4, further comprising: sealing the package.

* * * * *